United States Patent [19]

Kuehn et al.

[11] Patent Number: 5,194,629
[45] Date of Patent: Mar. 16, 1993

[54] PROCESS FOR PRODUCING N-TERTIARY BUTOXYCARBONYL-MALEINIMIDE

[75] Inventors: Eberhard Kuehn, Hemhofen; Juergen Beck, Erlangen; Hellmut Ahne, Roettenbach; Siegfried Birkle, Hoechstadt A/Aisch; Rainer Leuschner, Erlangen; Michael Sebald, Hessdorf-Hannberg; Recai Sezi, Roettenbach; Hans-Juergen Bestmann, Erlangen, all of Fed. Rep. of Germany

[73] Assignee: Siemens Aktiengesellschaft, München, Fed. Rep. of Germany

[21] Appl. No.: 812,582

[22] Filed: Dec. 20, 1991

[30] Foreign Application Priority Data

Dec. 20, 1990 [DE] Fed. Rep. of Germany ....... 4040999

[51] Int. Cl.$^5$ ............................................. C07D 207/24
[52] U.S. Cl. .................................................... 548/531
[58] Field of Search .......................................... 548/531

[56] References Cited

U.S. PATENT DOCUMENTS

| | | | |
|---|---|---|---|
| 4,725,680 | 2/1988 | Barcelo et al. | 548/531 X |
| 4,775,609 | 10/1988 | McFarland | 430/325 |
| 4,827,124 | 6/1989 | Wu et al. | 430/270 |
| 4,912,018 | 3/1990 | Osuch et al. | 430/270 |
| 4,968,581 | 11/1990 | Wu et al. | 430/192 |

OTHER PUBLICATIONS

*Chemical Abstracts,* vol. 83 (1975) No. 28548X "Preparation and Some Properties of Maleimido Acids and Maleoyl Derivatives of Peptides", Keller et al.

"A Mild Two-Step Method for the Hydrolysis/Methanolysis of Secondary Amides and Lactams" 48, J. Org. Chem. pp. 2424–2426 (1983), Flynn, et al.

Y96 Applied Chemistry, pp. 291–292 (1984), Grehn, et al. Angew. Chem.

*Primary Examiner*—Joseph Paul Brust
*Attorney, Agent, or Firm*—Kenyon & Kenyon

[57] ABSTRACT

To produce N-tertiary butoxycarbonyl-maleinimide, maleinimide is reacted in the presence of a heterocyclic nitrogen compound having at least one tertiary nitrogen atom (as a base) with a more or less equimolar quantity of di-tertiary butyl-dicarbonate in a suitable solvent at temperatures of up to about 80° C.

8 Claims, No Drawings

PROCESS FOR PRODUCING N-TERTIARY BUTOXYCARBONYL-MALEINIMIDE

BACKGROUND OF THE INVENTION

1. Field of the Invention

The invention relates to a process for producing N-tertiary butoxycarbonyl-maleinimide (N-tert-butoxycarbonyl-maleimide).

2. Description of Related Art

The compound N-tertiary butoxycarbonyl-maleinimide is referred to in U.S. Pat. Nos. 4,837,124 and 4,912,018. It is explained therein (cf. Example 22) that this compound is copolymerized together with styrol; an N-tertiary butoxycarbonyl-maleinimide/styrol copolymer is formed in the course of this reaction (cf. also U.S. Pat. No. 4,775,609). However, a process for producing the monomer is not disclosed. Furthermore there is no other mention of the monomer nor of a process for producing it in the related scientific literature.

SUMMARY OF THE INVENTION

The object of the invention is to provide a process with which the monomeric compound N-tertiary butoxycarbonyl-maleinimide can be synthesized.

This is achieved according to the invention by reacting maleinimide in the presence of a heterocyclic nitrogen compound having at least one tertiary nitrogen atom (as a base) with about an equimolar quantity of di-tertiary butyl-dicarbonate in a suitable solvent at temperatures of up to about 80° C.

DETAILED DESCRIPTION OF THE INVENTION

According to the process of the invention, maleinimide is reacted with about equimolar quantities of di-tertiary butyldicarbonate, that is with equimolar quantities or with a slight excess. Di-tertiary butyl-dicarbonate is an ester of the hypothetical dicarbonic acid of the formula R*—O—CO—O—CO—O—R* (where R=C(CH$_3$)$_3$) and is used to introduce the tertiary butoxycarbonyl group —CO—O—C(CH$_3$)$_3$ (Boc group).

The reaction between maleinimide, whereby substituted maleinimides, in particular alkyl maleinimides, can also find application, and di-tertiary butyl-dicarbonate (Boc$_2$O) takes place in the presence of a base. It is important that initially Boc$_2$O and then the base are added to the maleinimide. Another important feature of the process according to the invention lies in the application of a special base. This base is a heterocyclic nitrogen compound having at least one tertiary nitrogen atom, that is a tertiary amino function. Mixtures of these types of compounds can also be used as a base.

The nitrogen heterocycle can be a 5- or 6-ring one, where a polycyclic structure can also exist. It can have an aromatic character, and can also contain other heteroatoms, such as O, S, P and Si. Furthermore, it can support substituents, such as alkyl and halogen groups, as well as exocyclic tertiary amino groups. On the other hand, primary and secondary amino groups impair the effectiveness of the base. The requisite amount of base is dependent upon its structure; it ranges from catalytic quantities, for example of ≦0.1 wt-%, up to equimolar quantities.

The base applied in the process according to the invention preferably exhibits one of the following structures:

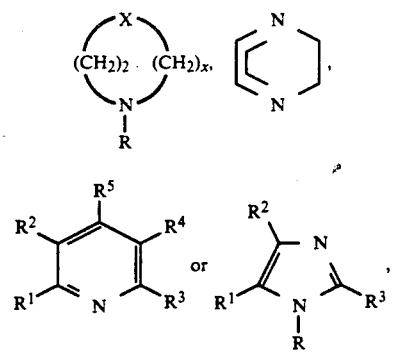

where the following applies:
x=1 to 2;
X=O, S, NR, PR or SiR$_2$;
R=alkyl with 1 to 10 C atoms;
R$^1$, R$^2$, R$^3$ and R$^4$=H, alkyl with 1 to 10 C atoms, where R$^1$ and R$^2$ or R$^3$ and R$^4$ can be cyclically linked to one another, or halogen, in particular F, Cl and Br; and
R$^5$=H or NR$_2$.

Preferably pyridine, 4-dialkylaminopyridines, N-alkylimidazoles, N-alkyl-morpholines and 1,4-diazabicyclo[2,2,2]octane are applied as a base. In addition, quinazoline (benzopyrimidine) and quinoxaline (benzopyrazine) as well as hexamethylenetetramine (1,3,5,7-tetraazaadamantane) also come under consideration, for example.

The reaction of maleinimide with Boc$_2$O takes place at temperatures of more or less up to 80° C. This reaction is preferably carried out at room temperature, however, it can also take place at temperatures of between 50° and 80° C., for example. The duration of the reaction amounts to >1 minute; generally the reaction time is between 1 and 2 hours.

The reaction between maleinimide and Boc$_2$O is carried out in a solvent. An organic solvent is preferably used. However, aqueous systems can also be used, such as dioxan/water mixtures. As organic solvents, chloroform, carbon tetrachloride, dimethylformamide, and tetrahydrofuran advantageously find application. In addition, methylene chloride, ethyl acetate and N-methylpyrrolidone, can also be used, for example.

After the reaction, the reaction mixture is processed according to generally known methods, and the reaction product is isolated and purified. The N-tertiary butoxycarbonyl-maleinimide (N-Boc-maleinimide) is thereby obtained in the form of colorless crystals with a melting point of 62.5° C. The structure of this compound is verified through elemental analysis as well as by means of NMR-, IR- and mass spectra.

Through the invention, a simple synthesis process is made ready for N-Boc-maleinimide, which produces this compound in a pure form and with a high yield. The monomeric N-Boc-maleinimide is particularly suited for polymer syntheses, particularly for producing N-Boc-maleinimide homopolymers. These types of homopolymers are in fact described (cf. U.S. Pat. No. 4,775,609), however a process for producing the polymers is not indicated. N-tertiary butoxycarbonyl-maleinimide can also be used to produce copolymers which find application in photoresists; cf. German Patent Application No. P 40 40 998.8.

Up until now, producing monomeric N-Boc imides, such as N-Boc-maleinimide, has not been described; all that has been described is the production of N-Boc derivatives of lactams and of secondary amides (cf.: *J. Oro. Chem.*, vol. 48 (1983), pp. 2424-2426) as well as of N-Boc pyrroles (cf.: *Applied Chem.*, vol. 96 (1984 , pp. 291 and 292). In this case, the triethylamine/4-dimethylaminopyridine (NEt$_3$/DMAP) system is employed as a base. However, this system is not suited for the process according to the invention. It has been shown, that N-Boc maleinimide cannot be produced by reacting maleinimide with Boc$_2$O in the presence of tertiary amines, such as triethyl amine and dimethylaniline. N-Boc pyrroles can in fact also be produced without triethyl amine; in this case, DMAP and Boc$_2$O are added to a solution of a pyrrole in anhydrous acetonitrile. However, this procedure is not successful for N-Boc maleinimide. Instead, in this case, the maleinimide is polymerized.

The invention shall be clarified in greater detail based on following examples for producing N-Boc maleinimide.

EXAMPLE 1

10 g of maleinimide (0.1 mol) and 24 g di-tertiary butyl-dicarbonate (0.11 mol) are placed in 100 ml chloroform under argon as a protective gas. 78.5 mg 4-dimethylaminopyridine (0.001 mol) are added to this solution; the mixture is then stirred for 4 hours at room temperature. It is then extracted by shaking two times with water and sodium hydrogencarbonate solution, in each case, and again with water; the combined organic phases are then dried over magnesium sulfate. The solvent is subsequently removed, and the residue is suspended in hot petroleum ether (60° to 80° C). The crystallizate that separates out when the suspension is cooled (in an ice bath) is sucked off and dried. The resulting mixture is sublimated (75°/3×0.02 torr), whereby colorless N-Boc-maleinimide is obtained; yield: 16.8 g (82.8% of the theory); Mr=197.2 g/mol; melting point: 62.5° C.

EXAMPLE 2

10 g of maleinimide (0.1 mol) and 24 g di-tertiary butyl-dicarbonate (0.11 mol) are placed in 100 ml dimethylformamide under argon as a protective gas. 78.5 mg 4-dimethylaminopyridine (0.001 mol) are added to this solution; the mixture is then stirred for 1 h at room temperature. The solution is subsequently concentrated by evaporation and petroleum ether is added to it with 2.5 times the volume; the N-Boc-maleinimide then separates out. The product is filtered off, dried and sublimated; yield: 17.2 g (85% of the theory); melting point: 62.5° C.

EXAMPLE 3

10 g of maleinimide (0.1 mol) and 22 g di-tertiary butyl-dicarbonate (0.1 mol) are placed in 100 ml tetrahydrofuran under argon as a protective gas. 8 ml pyridine (0.1 mol) are added to this solution; the mixture is then stirred for 24 h at room temperature. The volatile components are subsequently removed at the rotatory film evaporator (at 35°) and in the water-jet vacuum pump. 200 ml water are added to the residue and the residue is extracted by shaking three times, in each case with 100 ml methylene chloride. The combined organic phases are then washed in each case with 100 ml water, 5% sodium hydrogencarbonate solution and once again with water. After drying the organic phase with sodium sulfate, the solvent is removed. The brown residue is suspended in 100 ml hot petroleum ether (60° to 80° C.). The crystallizate that separates out when the suspension is cooled (in an ice bath) is sucked off an dried. The obtained mixture is sublimated (75°/3×0.02 torr), whereby colorless N-Boc-maleinimide is obtained; yield: 18.8 g (92.8% of the theory); Mr=197.2 g/mol; melting point: 62.5° C. The spectroscopic data ($^1$H-NMR, $^{13}$C-NMR, IR, UV and MS) confirm the structure.

EXAMPLE 4

1 g of maleinimide (0.01 mol), 2.2 g di-tertiary butyl-dicarbonate (0.01 mol), 1.2 g N-ethylmorpholine (0.01 mol) and 10 ml carbon tetrachloride are mixed together analogously to examples 1 through 3, and are then heated for 6 h to a temperature of 60° C.; the maleinimide hen dissolves. After cooling, the solution is extracted by shaking with water and then concentrated by evaporation. The resulting crystallizate is isolated and recystallized out of petroleum ether; yield: 1.61 g (81.5% of the theory); melting point: 62.5° C.

What is claimed is:

1. A process for producing N-tertiary butoxycarbonyl-maleinimide, comprising the step of reacting maleinimide in the presence of a base, which is a heterocyclic nitrogen compound having at least one tertiary nitrogen atom, with about an equimolar quantity of di-tertiary butyl-dicarbonate in a solvent at temperatures of up to about 80° C. for a duration grater than one minute, wherein the reaction is carried out by first combining the di-tertiary butyl-dicarbonate with the maleinimide followed by addition of the base.

2. The process according to claim 1, wherein the base is at least one of:

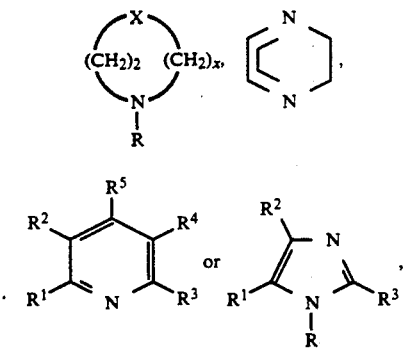

where the following applies:
x=1 or 2;
X=O, S, NR, PR or SiR$_2$;
R=alkyl with 1 to 10 C atoms;
R$^1$, R$^2$, R$^3$ and R$^4$=H, alkyl with 1 to 10 C atoms, where R$^1$ and R$^2$ or R$^3$ and R$^4$ can be cyclically linked to one another, or halogen; and
R$^5$=H or NR$_2$.

3. The process according to claim 2, wherein the base is at least one of pyridine, 4-dialkylaminopyridine, N-alkyl-imidazole, N-alkyl-morpholine and 1,4-diazabicyclo[2,2,2]octane.

4. The process according to claim 1 wherein the reaction is carried out at room temperature.

5. The process according to claim 2 wherein the reaction is carried out at room temperature.

6. The process according to claim 3 the reaction is carried out at room temperature.

7. The process according to claim 1 wherein the solvent is organic.

8. The process according to claim 7, wherein the solvent is selected from the group consisting of chloroform, carbon tetrachloride, dimethyl formamide, and tetrahydrofuran.

* * * * *